United States Patent [19]

Montagnier et al.

[11] Patent Number: 5,173,400
[45] Date of Patent: Dec. 22, 1992

[54] ANTIBODY DETECTION OF ANTIBODIES TO VIRAL PROTEINS IN SERUM

[75] Inventors: Luc Montagnier, Le-Plessis-Robinson; Jean C. Chermann, Elancourt; Francoise Barre-Sinoussi, Issy Les Moulineaus; Francoise Vezinet-Brun, Paris; Christine Rouzioux, Paris; Willy Rozenbaum, Paris; Charles Dauguet, Paris; Jacqueline Gruest, L'Hay Les Roses; Marie Theresa Nugeyre, Paris; Francoise Rey, Paris; Claudine Axler-Blin, Paris; Solange Chamaret, Paris, all of France

[73] Assignee: Institut Pasteur, France

[21] Appl. No.: 780,572

[22] Filed: Oct. 22, 1991

Related U.S. Application Data

[63] Continuation of Ser. No. 159,430, Feb. 17, 1988, abandoned, which is a continuation of Ser. No. 914,198, Oct. 1, 1986, abandoned, which is a continuation of Ser. No. 712,958, Mar. 18, 1985, abandoned, which is a continuation-in-part of Ser. No. 558,109, Dec. 5, 1983, abandoned.

[30] Foreign Application Priority Data

Sep. 15, 1983 [GB] United Kingdom ............... 83/24800

[51] Int. Cl.$^5$ ............................................... C12Q 1/70
[52] U.S. Cl. ......................................... 435/5; 435/7.1; 435/974
[58] Field of Search .................... 530/324, 345; 435/5, 435/7.1, 7.23

[56] References Cited

U.S. PATENT DOCUMENTS

| | | |
|---|---|---|
| 4,520,113 | 5/1985 | Gallo .................................. 436/504 |
| 4,629,783 | 12/1986 | Cosand ................................ 530/324 |
| 4,708,818 | 11/1987 | Montagnier et al. . |
| 4,751,180 | 6/1988 | Cousens et al. ...................... 435/68 |
| 4,784,941 | 11/1988 | Watanabe et al. ........................ 435/5 |
| 4,843,011 | 6/1989 | Sarngadharan et al. ....... 435/240.27 |

FOREIGN PATENT DOCUMENTS

| | | |
|---|---|---|
| 0138667 | 4/1985 | European Pat. Off. ................. 435/5 |
| 3636540 | 10/1986 | Fed. Rep. of Germany .......... 435/5 |
| WO86/04336 | 7/1986 | World Int. Prop. O. ............... 435/5 |

OTHER PUBLICATIONS

Barre-Sinoussi et al., "Analysis and Immunological Properties of Lymphadenopathy Associated Virus (LAV) Structural Proteins", Retroviruses Hum. Pathol. Int. Symp. Meeting Date 1984, 343–51.

Ferns et al., "Characterization of Monoclonal Antibodies Agaiinst the Human Immunodeficiency Virus (HIV) gag Products and Their Use in Monitoring HIV Isolate Variation" J. Gen. Virol., 68(1987) 1543–51.

Krause et al., "Isolation of human immunodeficiency virus-related simian immunodeficiency viruses from African green monkeys," Proc. Natl. Acad. Sci. USA, 86 (1989) 2892–96.

Chassogne et al., "A Monoclonal Antibody Against LAV GAG Precursor: Use For Viral Protein Analysis and Analysis and Antigenic Expression in Infected Cells," J. Immunol. 136(1986) 1442–45.

Van de Perre et al., "Detection of p17 Antigen in lymphocytes but not epithelial cells from cervicovaginal secretions of women seropositive for HIV: implications for heterosexual transmission of the virus", Genitourin. Med., 64(1988) 30–33.

Nature, vol. 313, pp. 636–637. Feb. 21, 1985.

Science, vol. 232, pp. 685–800, May 9, 1986.

Barré-Simoussi, F. et al., Science 220:868–871 (May 1983).

Montagnier, L. et al., Human T-cell Leukemia Lymphoma Viruses, Cold Spring Harbor Laboratories, C.S.H., NY (1984).

Gallo, R. C. et al., eds; oral presentation Sep. 14–16, 1983.

Montagnier, L. et al., Science 225:63–66 (Jul. 1984).

Montagnier, L. et al., Virology, 144:283–289 (1985).

L. Montagnier et al., "A New Type of Retrovirus Isolated From Patients Presenting With Lymphadenopathy And Acquired Immune Deficiency: Structural And Antigenic Relatedness With Equine Infectious Anaemia Virus," Ann. Virol. (Inst. Pasteur) 1984, 135 E, 119–134.

*Primary Examiner*—Christine M. Nucker
*Assistant Examiner*—Jeffrey Stucker
*Attorney, Agent, or Firm*—Finnegan, Henderson, Farabow, Garrett & Dunner

[57] ABSTRACT

Protein compositions containing the p18 and p25 proteins of the lymphadenopathy virus are used for detecting antibodies in blood serum as indicative of infection by such virus. The proteins can be used in various conventional ways to perform immunoassays for the detection of the antibodies.

9 Claims, No Drawings

ANTIBODY DETECTION OF ANTIBODIES TO VIRAL PROTEINS IN SERUM

This application is a continuation of application Ser. Nos. 07/159,430, filed Feb. 17, 1988, which is a continuation of U.S. Ser. No. 06/914,198, filed Oct. 1, 1986, which is a continuation of U.S. Ser. No. 06/712,959, filed Mar. 18, 1985, which is a continuation-in-part of U.S. Ser. No. 06/558,109, filed Dec. 5, 1983 all now abandoned.

BACKGROUND OF THE INVENTION

1. Field of the Invention

Retroviruses as the vectors of human diseases have only recently been established. The first retrovirus shown to cause cancer was the human T-lymphoma/leukemia virus-I (HTLV-I). Poiosz et al., Proc. Nat'l. Acad. Sci. (1980), 77, 6815. A second retrovirus was reported as being present in hairy cell leukemia cells and was referred to as HTLV-II. Kalyanaraman et al., ibid. (1982) 218:571. These two viruses are capable of transformation, have a T-cell tropism and a reverse transcriptase requirement for magnesium.

With lymphadenopathy syndrome (LAS) or acquired immune deficiency syndrome (AIDS) becoming a major health threat, substantial efforts have been made to determine the cause of the disease. The syndrome differed from the diseases caused by the human retroviruses HTLV-I and HTLV-II, in that the agent did not transform the host cells to a neoplastic state, but rather was cytotoxic to the host cells. It shared a similar property to the earlier discovered retroviruses in having a T-cell tropism, particularly helper cells. It was early found that the syndrome could be transmitted by blood transfusions. A carrier of the disease who was a source of blood could be a transmitter of the disease to a person receiving that blood. It has, therefore, become a major effort to find ways to screen blood to detect whether the donor may have been infected with the pathogenic cause of the disease.

2. Description of the Art

Descriptions of LAV, HTLV-III and ARV may be found in Barre-Sinoussi et al., Science (1983) 220:868; Montagnier et al., Cold Spring Harbor Symposium (1984), in press; Vilmer et al., Lancet (1984) 1:753; Popovic et al., Science (1984) 224:497; Gallo et al., Science (1984) 224:500; Feorino et al., Science (1984) 225:69-72; Klatzman et al., Science (1984) 225:59-62; Montagnier et al., ibid. (1984) 225:63-66; Levy et al., Science (1984) 225:840-842; Montagnier et al., Ann. Virol. (Institut Pasteur 1984, 135E, 119-134; Kalyanaraman et al., Science (1984) 225:321; and Ray et al., Science (1984) 225:321; and Ray et al., Biochenm. and Biophys. Res. Comm. (1984) 121:126.

SUMMARY OF THE INVENTION

Methods and compositions are provided for detecting the presence of antibodies to proteins associated with lymphadenopathy virus (LAV). Particularly, the compositions contain at least one of the p18 or p25 proteins or immunologically active fragments thereof, and preferably contain both the p18 and p25 proteins, which are used in a reagent, either labeled or unlabeled, for the detection of serum antibodies to LAV or other immunogenically proteins as indicative of infection by LAV or related viruses.

DESCRIPTION OF SPECIFIC EMBODIMENTS

Methods and compositions are provided for detection of the probable incidence of infection with a T-cell tropic virus, whose infection in humans results in substantial diminution in the helper/suppressor T-cell ratio. The T-cell tropic retrovirus is characterized by having a density in a sucrose gradient of 1.16. The reverse transcriptase enzyme has a magnesium requirement with an optimal concentration of about 5 mM and an optimal pH of about 7.8. The reaction is not inhibited by actinomycin D. The reverse transcriptase activity displays a strong affinity for poly(adenylate-oligodeoxythymidylate).

Electron microscopy of ultrathin sections of virus-producing cells shows two types of particles, corresponding to the immature and mature forms of the virus. Immature particles bud at the cell surface with a dense crescent in close contact with the plasma membrane. Occasionally, some particles remain in this state, while being freed from the cell surface. Mature particles have a different morphology with a small, dense, eccentric core, mean diameter: 41 nm. Most of the virions are round (mean diameter: 139 nm) or ovoid, but in some instances, a tailed morphology can be observed. This latter form can be observed in cytoplasmic vesicles which are released in the media. Such particles are also formed by budding from vesicle membranes.

The retrovirus is tropic for helper T-lymphocytes (OKT4 cells). These cells are characterized in part by binding to monoclonal antibodies, such as those designated OKT4 (Ortho).

In most cases of the lymphotropic disease, the ratio of OKT4 cells to OKT8 cells, which is normally greater than 1, is depressed to values below 1, being 0.1 or less. More importantly, the absolute number of OKT4 cells per $mm^3$ of blood is severely reduced in these patients.

The subject retroviruses are immunologically distinct from the previously known HTLV-I. A monoclonal antibody to p19 of HTLV-I (Robert-Guroff et al., J. Exp. Med. (1981) 154:1957) and a polyclonal goat antibody to p24 of HTLV-I (Kalyanaraman et al., J. Virol (1981) 38:906) were used in an indirect fluorescence assay. Infected cells from the biopsy of a patient having the subject virus and lymphocytes obtained from a healthy donor and infected with the same virus were assayed. The virus-producing cells did not react with either antibody, whereas two lines of cord lymphocytes chronically infected with HTLV-I (Popovitch et al., Science (1983) 219:856) and used as controls showed strong surface fluorescence.

In addition, proteins detected on polyacrylamide gel electrophoresis of a lysate of cells infected with the subject virus included p13, p18, p25, p36, p42 and p80 proteins (the numbers indicate the approximate molecular weight in kilodaltons). The retroviruses of the subject invention are, therefore, those viruses producing the same or similar proteins where said same or similar proteins are substantially completely immunologically cross-reactive which said proteins detected in said lysate, particularly as to epitopic sites specific for p18 and p25 of LAV.

The subject method is therefore applicable to detection of infection in humans as a result of viruses having all or substantially all of the above characteristics and producing proteins cross-reactive with the p18 and p25 proteins observed with the subject LAV virus.

The compositions which are employed in the assays of the subject invention will have one or both, preferably both, the p18 and p25 proteins or immunologically active fragments thereof, either natually or synthetically derived, having epitopic sites specific for LAV. The p25 and p18 proteins appear to be core proteins. The compositions employed in the subject invention may be derived from a variety of sources, either naturally occurring or synthetic. At least 10% by weight, preferably at least 20% by weight, of the polypeptide present in the composition will be related to epitopic sites of the p18 and/or p25 proteins. Up to about 100% by weight of the polypeptides in the composition can be related to p18 or p25 proteins or mixtures thereof. Preferably, polypeptides related to both p18 and p25 proteins will be present in the composition in an amount of at least about 15 percent by weight and up to about 100% by weight. Frequently, polypeptides related to both p18 and p25 proteins will not be more than about 65% by weight. Amounts of the p18 or p25 proteins or mixtures thereof may be employed in the lower portion of the range where the other proteins present in the protein composition are derived from or related to epitopic sites associated with the subject virus.

The retroviral composition may be purified by any conventional technique, e.g., density gradient separation. The polypeptide compositions employed in the assay may come from a lysate prepared by treating a substantially purified viral composition with a detergent or other chaotropic agent to disaggregate the proteins. The resulting lysate may be further purified by chromatography, e.g., affinity chromatography, electrophoresis, or the like. Individual components from the lysate, when separated, can be recombined to provide for substantially the same or different proportions of the different polypeptide components. The compositions will be at least substantially free of polypeptides resulting from expression of structural genes of the human genome, where the expression is unrelated to the retroviral infection.

Alternatively, all or portions of the viral RNA may be reverse transcribed to provide single-stranded DNA (ss DNA), which can be used as a template to provide double-stranded DNA (ds DNA). The ds DNA can be introduced into an appropriate mammalian vector for introduction into a compatible host for expression of some or all of the viral proteins. Alternatively, one or more structural genes of the virus may be identified, ds DNA prepared from the RNA encoding for such structural gene and introduced into a prokaryotic or eukaryotic expression vector having the appropriate transciptional and translational initiation and termination signal sequences for expression. For glycoproteins it will usually be desirable to employ a host which provides for appropriate glycosylation, so as to maximize the immunologic similarity of the glycoprotein produced by recombinant techniques, as compared to the naturally occurring glycoprotein.

The related oligopeptides having epitopic sites of p18 and/or p25 (which may be on the same or different molecules) will be of at least 12 amino acids, more usually at least 18 amino acids, and may be 30 amino acids or more, up to and exceeding the number of amino acids of the parent polypeptide. These oligopeptides may be synthesized chemically, by cloning, or as fragments of larger polypeptide precursors. The oligopeptides may be joined to longer proteins in some instances.

The subject protein compositions can be employed in any of a variety of conventional immunoassays. These assays employ a wide variety of labels and provide for a varying range of sensitivity and susceptibility to interference. Labels include radionuclides, enzymes, fluorescers, chemiluminescers, particles, ligands, enzyme substrates, enzyme cofactors, enzyme inhibitors, particularly suicide inhibitors, light emitter-quencher combinations, etc. The immunoassays may be homogeneous or heterogeneous, where the distinction relates to the use of a separation step for separating uncomplexed label from complexed label.

Depending upon the protocol, the protein composition of the subject invention may be labeled or unlabeled. For example, the p18-p25 protein composition may be covalently or non-covalently bound to the surface of a microtiter plate well. A serum sample suspected of containing antibody may then be added, unbound antibody washed away and either labeled anti-human IgG or labeled p18-p25 composiiton added. The advantage of the latter is that it provides for a lower amount of non-specific binding of the label. Thus, either the anti-human IgG or the p18-p25 protein composition may be labeled with radionuclides, enzymes, or the like and the signal detected in accordance with conventional techniques. Various radioisotopes include $^{35}S$, $^{32}P$, $^{125}I$, $^{3}H$ $^{152}Eu$, etc. For enzymes, a variety of enzymes can be used, such as horseradish peroxidase, glucose-6-phosphate dehydrogenase, glucose oxidase, alkaline phosphatase, $\beta$-galactosidase and the like. A wide variety of substrates are available which allow for colorimetric or fluorimetric detection. For fluorescers, fluorescein, dansyl, rhodamine, Texas red, phycobiliproteins, or the like may be employed. The choice of the assay method will primarily depend upon the sensitivity desired, the convenience of the assay, and the availability of the reagents.

Conveniently, kits can be provided having the subject protein compositions in conjunction with the appropriate reagents. The appropriate reagents may include labeled protein compositions, labeled anti-human immunoglobulin, or labeled anti-p18 and/or anti-p25. In addition, as a control, a lymphocyte extract obtained from a healthy person may be provided, as well as serum from a healthy person for standards. In addition, buffers, stabilizers, or other ancillary additives may also be included. The materials will normally be provided as lyophilized compositions, which can be reconstituted to the desired concentrations. In addition, depending upon the particular protocol, other materials may be provided, such as enzyme substrates, cofactors, or the like.

Where reagents are combined, they will normally be in proportion to at least substantially maximize the sensitivity of the assay. Where the active reagents are in separate containers, the proportions will be in part a matter of convenience, since each will be reconstituted in a prescribed volume to be in appropriate relative proportion with the volumes of the other reagents.

The following examples are offered by way of illustration and not by way of limitation.

EXPERIMENTAL

1. Virus Propagation

Cultured T-lymphocytes from either umbilical cord peripheral blood, or bone marrow cells from healthy, virus negative, adult donors are suitable for virus propagation.

There is, however, some variation from individual to individual in the capacity of lymphocytes to grow the virus. Therefore, it is preferable to select an adult healthy donor, who had no antibodies against the virus, as detected by reverse transcriptase activity (RT), nor expressed viral proteins.

Lymphocytes of the donor were obtained and separated by cytophoresis and stored until used frozen at −180° C. in liquid nitrogen, in RPMI 1640 medium, supplemented with 50% decomplemented human serum and 10% DMSO.

For viral infection, lymphocytes were put in culture (RPMI 1640 medium) with phytohaemagglutinin (PHA) at a concentration of $5 \times 10^6$ cells/ml for three days. The medium was then removed and cells resuspended in viral suspension (crude supernatant of virus-producing lymphocytes, stored at −80° C.). Optimal conditions of cell/virus concentrations were $2 \times 10^6$ cells for 5 to 10,000 cpm of RT activity, the latter determined as follows.

The cell-free supernantant was ultra-centrifuged for 1 hr at 50,000 rev/min. The pellet was resuspended in 200 ul of NTE buffer (10 mM Tris, pH 7.4, 100 mM NaCl, and 1 mM EDTA) and was centrifuged over a 3 ml linear sucrose gradient (10 to 60 percent) at 55,000 rev/min for 90 min in an IEC type SB 498 rotor. Fractions (200 ul) were collected, and 30 ul samples of each fraction were assayed for DNA RNA-dependent polymerase activity with 5 mM $Mg^{2+}$ and poly(a)-oligo-(dT)$_{12-18}$ as template primer. A 20 ul portion of each fraction was precipitated with 10% trichloroacetic acid and then filtered on a 0.45 um Millipore filter. The $^3$H-labeled acid precipitable material was measured in a Packard counter.

After 24 hr, cells were centrifuged to remove the unadsorbed virus and resuspended in culture PHA-free medium and supplemented with PHA-free TCGF (Interleukin 2): (0.5–1 U/ml, final concentration), Polybrene (Sigma) 2 ug/ml and sheep anti-interferon serum, inactivated at 56° C. for 30 min (0.1% of a serum which is able to neutralize 7 U of α leukocyte interferon at a 1/100,000 dilution).

Virus production was tested every 3 days by an RT activity determination on 1 ml samples.

The presence of anti-interferon serum is important in virus production. When lymphocytes were infected in the absence of anti-human-α-interferon serum, virus production, as assayed by RT activity, was very low or delayed. The sheep antiserum used was raised against partly purified α leukocyte interferon, made according to the Cantell technique.

Virus production starts usually from day 9 to 15 after infection, and lasts for 10–15 days. In no case was the emergence of a continuous permanent line observed.

2. VIRUS PURIFICATION

For its use in ELISA, the virus was concentrated by 10% polyethyleneglycol (PEG 6000) precipitation and banded twice to equilibrium in a 20–60% sucrose gradient. The viral band at density 1.16 was then recovered and used as such for ELISA assays.

For use in a radioimmunoprecipitation assay (RIPA), purification in isotonic gradients of METRIZAMIDE-/or NICODENZ (trademarks of Nyegaard, Oslo) were found to be preferable. Viral density in such gradients was very low (1.10–1.11).

Metabolic labeling with radioactively labeled amino acid $^{35}$S-methionine of cord lymphocyte cells and virus was carried out for 20 hr, the cells lysed with detergent, virus banded as described above, lysed with RIPA buffer in a medium deprived of the amino acid used for labeling, immunoprecipitated, followed by polyacrylamide gel electrophoresis, except the following modifications for RIPA: virus purified in Nycodenz was lysed in 4 volumes of RIPA buffer (0.5% SDS) containing 500 U/ml of aprotinin. Incubation with 5 ul of serum to be tested was made for 1 hr at 37° C. and then 18 hr at 4° C. Further incubation of the immunocomplexes with protein A Sepharose beads was for 3 hr at 4° C.

3. PREPARATION OF THE VIRUS EXTRACT FOR ELISA ASSAYS

Virus purified in a sucrose gradient, as above described, is lysed in RIPA buffer (0.5% SDS) and coated on wells of microtest plates (Nunc).

Preferred conditions for the ELISA assay are described hereafter.

After addition to duplicate wells of serial dilutions of each serum to be tested, the specifically fixed IgGs are revealed by goat anti-human IgG coupled with horseradish peroxidase. The enzymatic reaction is carried out on ortho-phenylenediamine (OPD) as substrate and read with an automatic spectrophotometer at 492 nm.

On the same plate each serum is tested on a control antigen (a crude cytoplasmic lysate of uninfected T-lymphocytes from the same donor) in order to eliminate non-specific binding, which can be high with some sera.

Sera are considered as positive (possessing antibodies against the virus) when the difference between O.D. against the viral antigen and O.D. against control cellular antigen was at least 0.30.

Method

This ELISA test is for detecting and titrating seric anti-retrovirus type LAV antibodies. It comprises carrying out a competition test between a viral antigen (cultivated on T-lymphocytes) and a control antigen constituted by a lysate of the same though non-infected lymphocytes.

The binding of the antibodies to the two antigens is revealed by the use of a human antiglobulin labeled with an enzyme which provides a detectable signal in conjunction with a suitable substrate.

Preparation of the viral antigen

The cell cultures which are used are T-lymphocytes of human origin which come from:
umbilical cord blood,
bone marrow,
blood of a healthy donor.

After infection of the cells by the virus, the supernatant of the infected cell culture is used. It is concentrated by precipitating with 10% PEG, then purified (two or three times) on a (20–60%) sucrose gradient by ultracentrifugation to equilibrium.

The viral fractions are gathered and concentrated by centrifugation at 50,000 rev/min for 60 min.

The sedimented virus is taken up in a minimum volume of NTE buffer (Tris 0.01M (pH 7.4), NaCl 0.1M, EDTA 0.001M). The protein concentration is determined by the Lowry method. The virus is then lysed by a (RIPA+SDS) buffer (0.5% final) for 15 min at 37° C.

Preparation of the control antigen

The non-infected lymphocytes are cultured according to the preceding conditions for from 5 to 10 days.

They are centrifuged at low speed and lysed in the RIPA buffer in the presence of 5% of Zymofren (Specia) (500 μ/ml). After a stay of 15 min at 4° C. with frequent stirrings with a vortex, the lysate is centrifuged at 10,000 rev/min. The supernatant constitutes the control antigen. The protein concentration is measured by the Lowry method.

Reagents
1-Plates=NUNC-special controlled ELISA
2-Buffer PBS: pH 7.5
3-TWEEN 20
4-Carbonate buffer: pH=9.6 ($CO_3Na_2$=0.2M) ($CO_3HNa$=0.2M)
5-Non-fetal calf serum: which is stored in frozen state (BIOPRO),
6-Bovine serum albumin (BSA) (SIGMA fraction V)
7-Human anti IgG (H+L) labeled with peroxidase (PASTEUR), in 1 ml tubes preserved at 4° C.
8-Washing buffer=PBS buffer, pH 7.5+0.05% TWEEN 20 Dilution of the conjugate is carried out at the dilution indicated in PBS buffer+-TWEEN 20 (0.5%)+(BSA), 0.5 g/100 ml
9-Dilution buffer of sera=PBS buffer+0.05% TWEEN 20+0.5 g BSA per 100 ml
10-Substrate=OPD
  Citrate buffer pH=5.6 trisodio citrate ($C_6H_5Na_3O_7$, $2H_2O$), 0.05M; citric acid ($C_6H_8O_7$, $1H_2O$), 0.05M.
  Hydrogen peroxide=at 30% (110 volumes)used at 0.03% when using citrate buffer.
  OPD-(SIGMA)=75 mg per 25 ml of buffer (freshly prepared).

Preparation of the plates

The plates which are used have 96 U-shaped wells (NUNC).

The distribution of antigens is as follows:
100 μl of the viral antigen diluted in carbonate buffer at pH 9.6, are deposited in each of the wells of rows 1-2-5-6-9-10
100 μl of the control antigen, diluted in carbonate buffer at pH 9.6, are deposited in each of the wells of rows 3-4-7-8-11-12.

The dilution of the viral antigen is titrated with each viral product. Several dilutions of viral antigen are tested and compared to positive and negative known controls (at several dilutions) and to human anti-IgG labeled with peroxidase, the latter also being tested at several dilutions.

As a rule, the protein concentration of the preparation is from 5 to 2.5 μg/ml. The same protein concentration is used for the control antigen.

The plates are covered with a plastic lid and are incubated overnight at 4° C.

They are then put once in distilled water and centrifuged. The wells are then filled with 300 μl of non-fetal calf serum at 20% in PBS buffer and incubated for 2 hr at 37° C. (covered plates). The plates are washed 3 times in PBS buffer with TWEEN 20, 0.5% (PBS-TWEEN buffer):
first washing 300 μl
second and third washing 200 μl/well.

The plates are carefully dried and sealed with an adhesive plastic film. They can be stored at −80° C.

ELISA reaction: antibody titer assay

After defrosting, the plates are washed 3 times in PBS-TWEEN. They are carefully dried.

The positive and negative control sera as well as the tested sera are diluted first in the tube, with PBS-TWEEN containing 0.5% BSA.

The chosen dilution is 1/40.
100 μl of each serum are deposited in duplicate on the viral antigen and in duplicate on the control antigen.

The same is carried out for the positive and negative diluted sera.

100 μl of PBS+TWEEN+BSA are introduced in two wells (viral antigen) and in two wells (control antigen) to form the conjugated controls.

The covered plates are incubated for 90 min at 37° C.
They are washed 4 times in PBS-TWEEN.
100 μl of human anti-IgG (labeled with peroxidase) at the choosen dilution are added to each well and incubated at 37° C.

The plates are again washed 5 times with PBS+TWEEN buffer and carefully dried.

The enzyme reaction is carried out with 100 μl OPD substrate (0.05% in citrate buffer pH 5.6 containing 0.03% of $H_2O_2$) in each well. The plates are left in a dark room for 20 min at room temperature. Reading is carried out on a spectrophotometer (for microplates) at 492 nm.

Sera deemed as containing antibodies against the virus are those which give an ODD (optical density difference=optical density of viral antigen less optical density of control antigen) equal to or higher than 0.30.

This technique enables a qualitative titration as well as a quantitative one. For this purpose, it is possible either to use several dilutions of the serum to be assayed or to compare a dilution of the serum with a range of controls tested under the same conditions.

The following table provides the results of serological investigations for LAV antibodies carried out by using the above exemplified ELISA assay.

TABLE

| | Results of Serological Investigations for LAV Antibodies | | |
|---|---|---|---|
| | Total examined | ELISA-LAV positive/% positive | ELISA-HTLV1+ (Biotech) positive/% positive |
| Lymphadenopathy patients* | 35 | 22 (63) | 5** (14) |
| Healthy homosexuals | 40 | 7 (17) | 1 (3) |
| Control population | 54 | 1 (1.9) | 0 (<2.6) |

*28 homosexuals, 3 Haitians (1 woman), 4 toxicomans (2 women)
+The number of positive sera is probably overestimated in this test, since no control of non-specific binding could be done.
**Out of the 5 LAS HTLV1 positive, 3 were born in Haiti, 1 had stayed for a long time in Haiti and 1 had made several travels to USA. All of them also had antibodies against LAV.

The table shows clearly high prevalence of LAV antibodies in the homosexual patients with LAS, a very low incidence in the normal population and also a moderate spread of virus infection in still healthy homosexuals. In the latter group, all the positive individuals had a high number of partners (>50 per year). The groups of AIDS patients gave less interpretable results: approximately 20% had LAV antibodies, but some of the sera were taken at a very late stage of the disease, with a possible inhibition of the humoral response.

It should be further mentioned that lymphocytes of all LAS patients do not produce detectable amounts of LAV-type virus. Particularly cells of lymph nodes from 6 more LAS patients were put in culture and tested for virus production. No virus release could be detected by RT activity. However, a p25 protein recognized by the serum of the first patient could be detected in cytoplasmic extracts of the T-cells labeled with $^{35}$S-methionine in 3 other cases. This suggests partial expression of a similar virus in such cases. Moreover, all (6/6) of these patients had antibodies against LAV p25 protein, indicating that they all had been infected with a similar or identical virus.

The LAV1 virus has been deposited at the "Collection Nationale des Cultures de Micro-organismes" (C.N.C.M.) 28 rue du Docteur Roux, 75724 Paris Cedex 15, under No. I-232 on Jul. 15, 1983 and IDAV1 and IDAV2 viruses have been deposited at the C.N.C.M. on Sep. 15, 1983 under No. I-240 and I-241, respectively. The invention encompasses as well the extracts of mutants or variants of the above deposited strains as long as they possess substantially the same immunological properties.

A competitive RIA of the p25 protein of LAV and analogous core proteins of other retroviruses was carried out. The RIAs were carried out with $^{125}$I-labeled LAV p25 and limiting dilution of human serum positive for antibodies to LAV (B.R.U. patient). Serial dilutions (100 μl) of solubilized virus in buffer 1′ (20 mM disodio acid phosphate (pH 7.6), 2 mM NaCl, 1 mM EDTA, 0.3% Triton X-100, 0.1 mM phenylmethylsulfonyl fluoride, and bovine serum albumin (2 mg/ml) were incubated with the appropriate serum for 1 hr at 37° C. Labeled LAV p25 (8000 counts/min in 50 μl of buffer 1) was then added, and the mixture was further incubated at 37° C. and at 4° C. overnight. A 20-fold excess of goat antiserum to human IgG was then added and the volume made up to 1 ml in buffer 1. The samples were further incubated at 37° C. for 1 hr and at 4° C. for 2 hr and then centrifuged at 2500 rev/min for 5 min. The supernatant fluids were aspirated and the radioactivity in the sediment was determined in a gamma counter. It was found that unlabeled p25 from LAV competed well for homologous antibody (from patient B.R.U.) while other retroviruses did not. The non-competing viruses included HTLV-I, HTLV-II, Mason-Pfizer monkey virus, Simian sarcoma virus, baboon endogenous virus, Rauscher murine leukemia virus, mouse mammary tumor virus and equine infectious anemia virus.

Serum from AIDS patients was obtained either as part of various studies sponsored by the Centers for Disease Control (CDC) or as individual specimens submitted directly to CDC. Serum from LAS patients was obtained as part of an ongoing perspective study of the syndrome among homosexual men in Atlanta. Serum from CDC employees who worked in laboratories in other areas was obtained in 1983 and 1984; some of the laboratory workers were exposed to materials from AIDS patients. Serum samples were also collected from homosexual men, 18 years of age or older, who sought medical care at the San Francisco City Clinic. These samples were routinely collected from 1978 as part of ongoing studies of Hepatitis B virus infection in homosexual men; specimens from 1984 were obtained according to the same protocol as part of a Hepatitis B vaccine study. Serum from blood donors (provided by the National Red Cross) was chosen at random from samples obtained in 1980 and 1981.

Specific antibody to the core protein of LAV p25 was present in serum from 41% of the AIDS patients and from 72% of the LAS patients. No antibody was detected in serum from CDC employees or from the blood donors.

The prevalence of antibodies to LAV p25 varied only slightly among different groups of AIDS patients. There was considerable variation, however, among AIDS patients with different disease manifestations. Patients with Kaposi's sarcoma alone had a significantly higher antibody prevalence [22 (63%) of 35] compared with patients who had only opportunistic infections [29 (34%) of 90] (P=<0.005, Students t-test). These results are consistent with the observation that Kaposi's sarcoma patients are less immunodeficient that patients with opportunistic infections.

Antibodies to p18 have been detected in the sera of a majority of lymphadenopathy and AIDS patients by Western blotting and radioimmunoprecipitation assay. In general, Western blotting appears to be a more sensitive means of detecting antibody to p18 than is immunoprecipitation. Antibody to p18 also appears to be more prominent early in the disease course than late.

In accordance with the subject invention, compositions are provided which can be used in a wide variety of methods for screening serum for the presence of antibodies to the subject retrovirus. Thus, the subject compositions provide for protection against the presence of the retrovirus in serum for transfusion, in indicating the presence or prior existence of infection of the subject virus, and in providing means for distinguishing among the various T-cell tropic viruses.

Although the foregoing invention has been described in some detail by way of illustration and example for purposes of clarity of understanding, it will be obvious that certain changes and modifications may be practiced within the scope of the appended claims.

What is claimed is:

1. A diagnostic method for detecting the presence of antibodies that specifically bind to antigens of human immunodeficiency virus (HIV), comprising:
   (a) contacting a radioactively labeled lysate of HIV-1 comprising p18 antigen with a biological sample for a time and under conditions sufficient to permit formation of antigen-antibody complex between said p18 antigen and said antibodies; and
   (b) measuring the formation of said complex to determine the amount of p18 antigen present in the sample.

2. The method according to claim 1, wherein said biological sample is from a human.

3. The method according to claim 2, wherein said amount of p18 antigen present in the sample is used to determine the amount of p18 antigen present in the human.

4. The method according to claim 3, further comprising determining the amount of free complexing antibody to p18 antigen of HIV present in the human.

5. The method according to claim 1, further comprising
   (a) contacting a radioactively labeled lysate of HIV-1 comprising p25 antigen with a biological sample for a time and under conditions sufficient to permit formation of antigen-antibody complex between said p25 antigen and said antibodies; and
   (b) measuring the formation of said complex to determine the amount of p25 present in the sample.

6. The method according to claim 5, wherein said biological sample is from a human.

7. The method according to claim 6, wherein said amount of p18 antigen present in the sample is used to determine the amount of p18 antigen present in the human, and said amount of p25 antigen present in the sample is used to determine the amount of p25 antigen present in the human.

8. The method according to claim 6, wherein said amount of p25 antigen present in the sample is measured as a sum of the amount of p18 antigen and p25 antigen present in the sample.

9. The method according to claim 7, further comprising determining the amount of free complexing antibody to p18 antigen of HIV present in the human, and determining the amount of free complexing antibody to p25 antigen of HIV present in the human.

* * * * *